United States Patent [19]

Kawaguchi

[11] Patent Number: 4,912,962
[45] Date of Patent: Apr. 3, 1990

[54] METHOD OF DETECTION OF OSCILLATION PERIOD FOR OSCILLATORY DENSIMETER

[75] Inventor: Kenji Kawaguchi, Kyoto, Japan

[73] Assignee: Kyoto Electronics Manufacturing Co., Ltd., Kyoto, Japan

[21] Appl. No.: 326,507

[22] Filed: Mar. 21, 1989

Related U.S. Application Data

[63] Continuation of Ser. No. 143,252, Dec. 29, 1987, abandoned.

[30] Foreign Application Priority Data

Dec. 29, 1986 [JP] Japan ................................ 61-312914

[51] Int. Cl.[4] ............................................. G01N 9/00
[52] U.S. Cl. .................................................. 73/32 A
[58] Field of Search ............. 73/32 A, 30, 580, 861.38

[56] References Cited

U.S. PATENT DOCUMENTS 4,738,144 4/1988 Cage .................................. 73/861.38

OTHER PUBLICATIONS

H. Leopold et al., "The Application of the Mechanical Oscillator Technique for the Determination of the Density of Physiological Fluids," *Biomedizinische Technik*, vol. 22, No. 10 (1977), pp. 231–234.

*Primary Examiner*—John Chapman
*Attorney, Agent, or Firm*—Lowe, Price, LeBlanc, Becker & Shur

[57] ABSTRACT

An oscillation period of an oscillating tube of an oscillatory densimeter is detected while the oscillation of the oscillating tube is maintained by applying an external force in the form of a pulse signal to the oscillating tube in one direction each time the tube passes the original place in that direction so that a stable oscillation free from any influential distortion can be obtained.

10 Claims, 3 Drawing Sheets

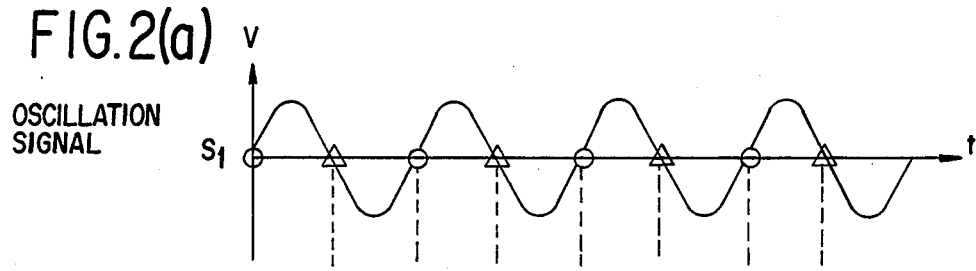
FIG. 2(a) OSCILLATION SIGNAL $S_1$
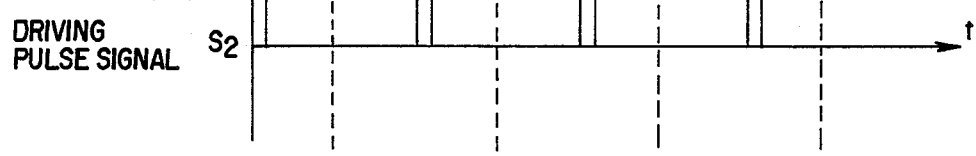
FIG. 2(b) DRIVING PULSE SIGNAL $S_2$
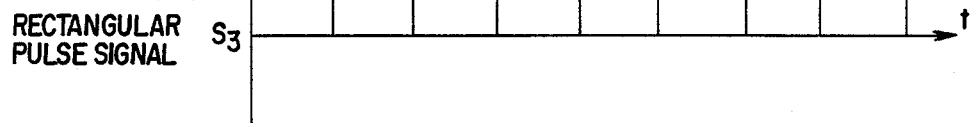
FIG. 2(c) RECTANGULAR PULSE SIGNAL $S_3$

FIG. 3 PRIOR ART
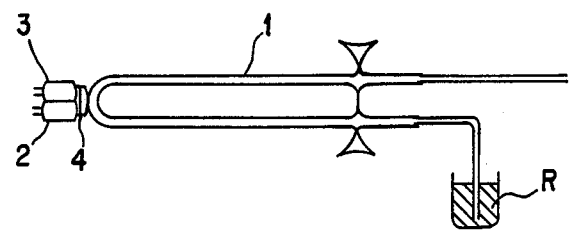
FIG. 4(a) PRIOR ART
FIG. 4(b) PRIOR ART
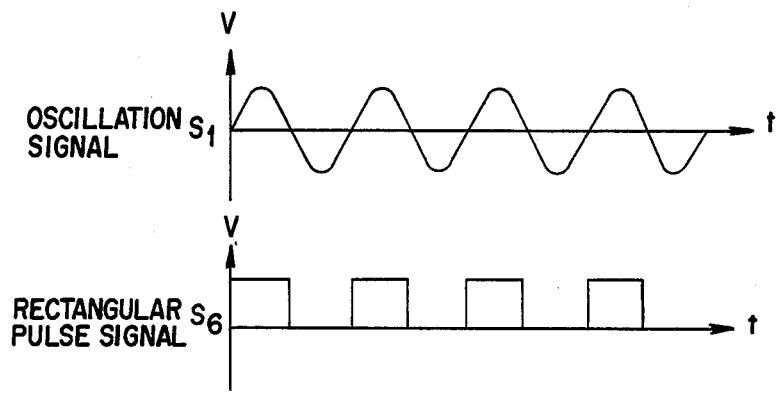

4,912,962

METHOD OF DETECTION OF OSCILLATION PERIOD FOR OSCILLATORY DENSIMETER

This application is a continuation of application Ser. No. 07/143,252, filed Dec. 29, 1987, now abandoned.

BACKGROUND OF THE INVENTION

The present invention relates to an oscillatory densimeter and in particular to a method of detecting an oscillation period of an oscillating tube of the oscillatory densimeter on the basis of an oscillation signal obtained by driving the oscillating tube.

The oscillatory densimeter is an instrument to measure densities of liquids which fill the oscillating tube on the basis of the oscillation period of the tube, for the oscillating period is determined depending on the densities of the liquids.

FIG. 3 is a schematic diagram illustrating an essential part of the oscillatory densimeter. Oscillating tube 1 is a thin, U-shaped tube filled with a liquid R for which density is to be measured. A magnet 4 is attached to oscillating tube 1, at the bottom of the U-shape. The oscillation period of tube 1 is detected through magnet 4 by a detection head 2 arranged against the magnet. As initial oscillation of oscillating tube 1 is very weak and soon attenuates, an external force must be applied to tube 1 so that a signal indicative of the oscillation can be maintained strong enough to be measured until the detection is completed. A driving head 3 arranged adjacent to detection head 2 applies the external force thereto to drive oscillating tube 1 on the basis of oscillation signal $S_1$ generated by detection head 2. Oscillation signal $S_1$ is an approximate sine wave as illustrated in FIG. 4(a) and applied to driving head 3 after being amplified as it is or shaped into a rectangular pulse signal as illustrated in FIG. 4(b). However, accuracy of the measurement may be deteriorated when oscillation signal $S_1$ is distorted or the phase thereof is not stable in comparison with a genuine sine wave.

Generally speaking, relation between density $\rho x$ of the liquids and oscillation period Tx is represented by an expression (1)

$$\rho_x = \rho_A \frac{T_A^2 - T_x^2}{T_A^2 - T_B^2} (\rho_A - \rho_B) \qquad (1)$$

wherein
$\rho x$: density of the substance of which density is to be measured
$\rho A$: density of a first reference substance A
$\rho B$: density of a second reference substance B
Tx: oscillation period of the substance of which density is to be measured
TA: oscillation period of the first reference substance A
TB: oscillation period of the second reference substance B This expression, however, is not always precisely applicable to the results obtained by the prior art as described above.

SUMMARY OF THE INVENTION

An object of the present invention is to provide a method of detecting the oscillation period of the oscillatory densimeter in which any distortion of the oscillation signal can be avoided as well as the stability of the oscillation signal is increased, so that expression (1) is always precisely applicable between the densities and oscillation periods and, therefore, correct densities of the liquids can be obtained.

To achieve the object, the oscillating tube is in the present invention driven by means of a pulse signal which is in synchronization with the oscillation of the tube. The pulse signal is applied to the tube in the same direction with the oscillation when voltage of the oscillation signal is 0 V. Each application is completed instantaneously. That is, the time for which the external force is applied to the tube is very short in each cycle of the oscillation. An extremely stable oscillation signal free from the distortion can be obtained as a result.

Pulse duration of the pulse signal may be constant without respect to the oscillation period, or may be changed in proportion to the period. When the pulse duration is fixed at a constant value, the structure of the apparatus of the invention can be made simple, although errors may be caused because the ratio of the pulse duration to the oscillation period is made variable by such fixation.

The driving pulse signal is a pulse train which rises in a positive or negative direction when the voltage of the oscillation signal is 0 V or, more specifically, when the oscillation of the tube transits from a negative half cycle to a positive half cycle or vice versa respectively. The other pulse trains will put the oscillation out of order.

In other words, the external driving force is applied to the oscillating tube instantaneously only when the oscillating tube is in the original place, or the oscillation is left as it is while the tube is displaced from the original place. As a result, an oscillation signal which is a genuine sine wave can be obtained, which significantly increases the accuracy of the measurement. The oscillation precisely maintains the relation as defined by expression (1) between the oscillation period and the density.

The effect of the present invention as described above can be further heightened by detecting the oscillation period 180° after the application of the external force.

Embodiments of the present invention will now be described with reference to the accompanying drawings, in which:

FIG. 2 is a timing chart of operation of the apparatus illustrated in FIG. 1.

FIG. 3 is a schematic diagram of a densimeter of the prior art.

FIG. 4 is a timing chart of the oscillation and driving signals used in the prior art.

DETAILED DESCRIPTION OF THE PREFERRED EMBODIMENTS OF THE INVENTION

Figure 1:
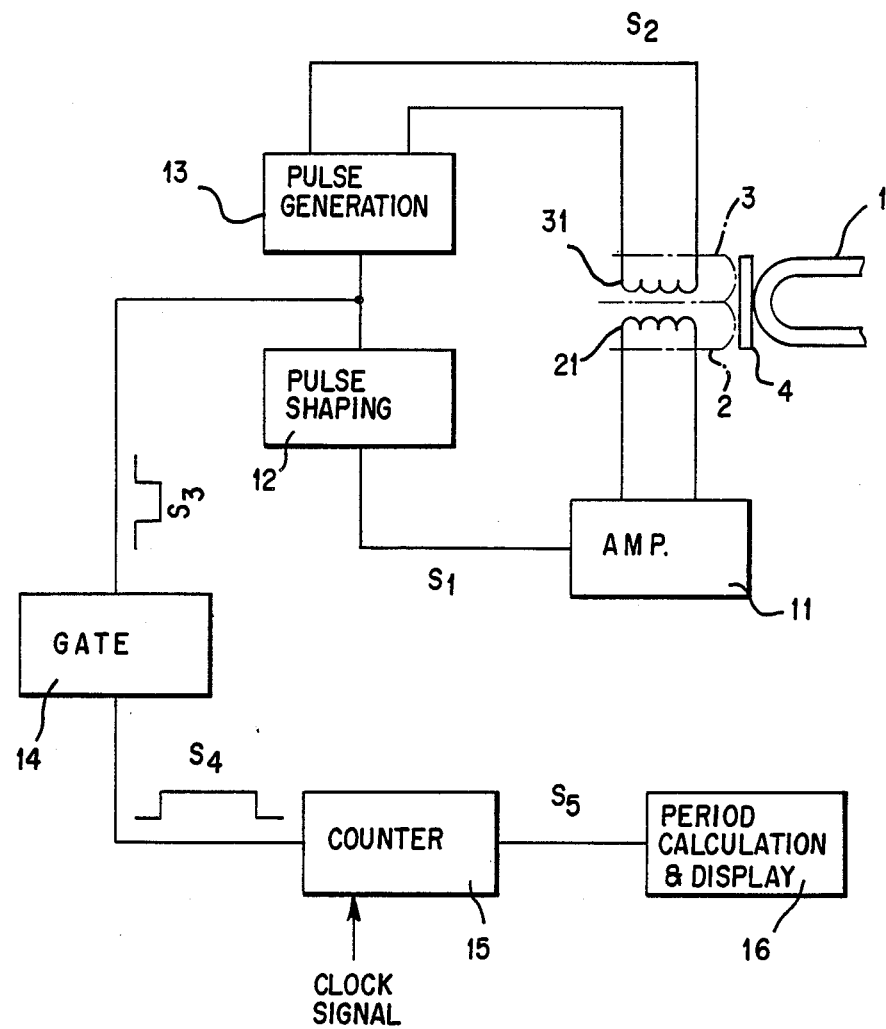
FIG. 1 is a block diagram of the apparatus to achieve the present invention.

With reference to FIGS. 1 and 2, oscillation signal $S_1$ as illustrated in FIG. 2(a) is generated by a detection coil 21 of detection head 2, indicating oscillation of oscillating tube 1 filled with the liquid for which density is to be measured. Oscillation signal $S_1$ is applied to a pulse-shaping circuit 12 after being amplified by an amplifier 11. An output of pulse-shaping circuit 12 is a rectangular pulse signal $S_3$ as illustrated in FIG. 2(c), which is in synchronization with oscillation signal $S_1$. Rectangular pulse signal $S_3$ has a lower voltage level while oscillation signal $S_1$ is positive and a higher one while signal $S_1$ is negative. Signal $S_3$ is applied to a pulse generator 13 which generates driving pulse signal $S_2$, of which leadingedges correspond to trailing edges of signal $S_3$. In other words, driving pulse signal $S_2$ is generated each second interval the voltage of oscillation signal $S_1$ is 0 V, or more specifically, simultaneously with each transition of oscillation signal $S_1$ from a negative half cycle to a positive one as illustrated in FIG. 2(b). Driving coil 31 of driving head 3 is provided with driving pulse signal $S_2$ to drive oscillating tube 1.

Generally speaking, an oscillating object, a pendulum for example, maintains a stable oscillation without attenuation by application of an appropriate external force in the direction in which the object is moving, at the precise time the displacement of the object is made zero. Oscillation signal $S_1$ is made a stable sine wave by the application of driving pulse signal $S_2$ as described above by the same reason.

Though the densities may be calculated making use of oscillation signal $S_1$ obtained as described above, they can be determined more accurately by another embodiment as follows. Oscillation signal $S_1$ can not help being very slightly distorted by an impulse caused by the application of driving pulse signal $S_2$. Oscillation signal $S_1$, on the other hand, can be considered as a completely accurately sine wave when the voltage of the signal returns to 0 V 180° after each application of driving pulse signal $S_2$, because there remains no considerable influence of the application. It will be understood from the preceeding description with reference to FIG. 2 that the return of the voltage to 0 V corresponds to a leading edge of rectangular pulse signal $S_3$. The densities can be determined more accurately by starting measurement of the oscillation periods in synchronization with the leading edge.

Explaining in detail, rectangular pulse signal $S_3$ is supplied to a gate circuit 14 in this embodiment. Signal $S_3$ is there converted into a second rectangular pulse signal $S_4$ of which period is a whole number N times as long as that of first signal $S_3$. A number S of clock pulses is counted by a counter 15 while the level of second rectangular pulse $S_4$ signal is high. Number S is divided by number N to determine the number of the clock pulses generated for one period of oscillation signal $S_1$. The period of oscillation signal $S_1$ is calculated on the basis of the quotient. The calculated value of the period is put into expression (1) at calculator 16 and the result of the calculation is displayed. As the leading edge of rectangulr pulse signal $S_3$ corresponds very precisely to the transition of oscillation signal $S_1$ from the positive half cycle to the negative one, very accurate densities can be obtained by the calculation.

Structure of the apparatus as illustrated in FIG. 1 relies on the prior art from gate circuit 14 to calculator 16. Though driving pulse signal $S_2$ is a pulse train which rises when oscillation signal $S_1$ transits from the negative half cycle to the positive one in the described embodiment, it will be understood without question that the signal can be another pulse train which falls at each transition of oscillation signal $S_1$ from the positive half cycle to the negative one.

The accuracy of the density measurement can be significantly increased by the method of the present invention because oscillation signal $S_1$, which is a very accurate sine wave free from any distortion or phase shift, can be obtained by using driving signal $S_2$ which is a pulse signal applied to the oscillating tube when the voltage of the oscillation signal is 0 V. As a result, expression (1) is always precisely applicable to the relationship between the densities and oscillation periods.

What we claim is:

1. A method of detecting an oscillation period of an oscillating tube filled with a liquid for which density is to be measured with an oscillatory densimeter, comprising the steps of:
   (a) detecting an oscillation signal indicative of oscillation of the oscillating tube, said oscillation varying as a function of density of the liquid in the tube;
   (b) generating a driving pulse signal in synchronization with said oscillation signal, which driving pulse signal increases in the same direction of the oscillation signal when the magnitude of said oscillation signal is substantially zero and which driving pulse signal is shorter than the period of a half-cycle of the oscillation signal;
   (c) driving the oscillating tube by means of said driving pulse signal, wherein the pulse duration of said driving pulse signal is substantially constant regardless of the oscillation period of the oscillating tube; and
   (d) measuring the oscillation period of the oscillation tube.

2. A method of detecting the oscillation period as recited in claim 1, wherein the pulse duration of said driving pulse signal is variable in proportion to the oscillation period of the oscillating tube.

3. The method of claim 1, wherein said driving pulse is generated electronically by detecting the oscillation signal with a detecting coil of a detection head.

4. A method of detecting an oscillation period of an oscillating tube filled with a liquid for which density is to be measured with an oscillatory densimeter, comprising the steps of:
   (a) detecting an oscillation signal indicative of oscillation of the oscillating tube;
   (b) generating a driving pulse signal in synchronization with said oscillation signal, which driving pulse signal increases in the same direction of the oscillation signal when the magnitude of said oscillating signal is substantially zero;
   (c) driving the oscillating tube by means of said driving pulse signal; and
   (d) starting measurement of the oscillation period of the oscillating tube when the voltage of said oscillation signal is substantially zero and 180° after application of said driving pulse signal.

5. A method of detecting the oscillation period as recited in claim 4, wherein the pulse duration of said driving pulse signal is substantially constant without respect to the oscillation period of the oscillating tube.

6. A method of detecting the oscillation period as recited in claim 4, wherein the pulse duration of said dirving pulse signal is variable in proportion to the oscillation period of the oscillating tube.

7. The method of claim 4, wherein said driving pulse is generated electronically by detecting the oscillation signal with a detecting coil of a detection head.

8. A method of detecting an oscillation period of an oscillating tube filled with a liquid for which density is to be measured with an oscillatory densimeter, comprising the steps of:
   (a) detecting an oscillation signal which corresponds to oscillation of the oscillating tube;
   (b) generating a first rectangular pulse signal of which pulse duration corresponds to one of a positive or negative half cycle of said oscillation signal;

(c) generating a driving pulse signal of which leading edges thereof correspond to trailing edges of said first rectangular pulse signal;
(d) driving the oscillating tube by applying said driving pulse signal thereto;
(e) starting measurement of the oscillation period of the oscillating tube in synchronization with a leading edge of said first rectangular pulse signal, of which phase is delayed by 180° from said application of the driving pulse signal.

9. A method of detecting the oscillation period as recited in claim 8 wherein a second rectangular pulse signal, of which pulse duration is N times larger than that of the first rectangular pulse signal, is obtained and a count number of clock pulses counted while the level of the second rectangular pulse signal is high is divided by said number N to determine the oscillation period.

10. The method of claim 8, wherein said driving pulse is generated electronically by detecting the oscillation signal with a detecting coil of a detection head.

* * * * *